(12) United States Patent
Lichtsteiner et al.

(10) Patent No.: US 9,925,170 B2
(45) Date of Patent: Mar. 27, 2018

(54) METHODS OF ADIPOLYSIS AND COMPOSITIONS USEFUL THEREIN

(71) Applicant: KYTHERA BIOPHARMACEUTICALS, INC., Calabasas, CA (US)

(72) Inventors: Serge Lichtsteiner, Calabasas, CA (US); Alain Vasserot, Calabasas, CA (US); Neil Poloso, Irvine, CA (US)

(73) Assignee: Kythera Biopharmaceuticals, Inc., Parsippany, NJ (US)

( * ) Notice: Subject to any disclaimer, the term of this patent is extended or adjusted under 35 U.S.C. 154(b) by 0 days.

(21) Appl. No.: 15/283,246

(22) Filed: Sep. 30, 2016

(65) Prior Publication Data

US 2017/0095447 A1  Apr. 6, 2017

Related U.S. Application Data

(60) Provisional application No. 62/236,037, filed on Oct. 1, 2015.

(51) Int. Cl.
| | |
|---|---|
| *A61K 31/405* | (2006.01) |
| *A61K 31/366* | (2006.01) |
| *A61K 45/06* | (2006.01) |
| *A61K 9/00* | (2006.01) |

(52) U.S. Cl.
CPC .......... *A61K 31/405* (2013.01); *A61K 9/0014* (2013.01); *A61K 9/0019* (2013.01); *A61K 31/366* (2013.01); *A61K 45/06* (2013.01)

(58) Field of Classification Search
CPC .. A61K 31/405; A61K 9/0014; A61K 9/0019; A61K 31/366; A61K 45/06
USPC ........................................................ 514/419
See application file for complete search history.

(56) References Cited

U.S. PATENT DOCUMENTS

| | | |
|---|---|---|
| 4,270,537 A | 6/1981 | Romaine |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,649,912 A | 7/1997 | Peterson |
| 5,704,911 A | 1/1998 | Parsons |
| 5,730,992 A | 3/1998 | Savion et al. |
| 5,891,083 A | 4/1999 | Capella et al. |
| 5,893,397 A | 4/1999 | Peterson et al. |
| 5,993,412 A | 11/1999 | Deily et al. |
| 6,126,947 A | 10/2000 | Savion et al. |

FOREIGN PATENT DOCUMENTS

| | | |
|---|---|---|
| EP | 2 550 968 A1 | 1/2013 |
| EP | 2 923 698 A1 | 9/2015 |
| WO | WO 1997/013537 | 4/1997 |
| WO | WO 1997/037705 | 10/1997 |
| WO | WO 1999/034850 | 7/1999 |
| WO | WO 2004/052368 A1 | 6/2004 |

OTHER PUBLICATIONS

Williams et al. Journal of Lipid Research, 1992, 33, 193.*
International Search Report and Written Opinion, PCT/US2016/055057, Kythera Biopharmaceuticals, Inc., 12 pages (Jan. 16, 2017).

* cited by examiner

*Primary Examiner* — Yevegeny Valenrod
(74) *Attorney, Agent, or Firm* — Foley & Lardner LLP

(57) ABSTRACT

Provided herein are pharmacologically active compositions suitable for topical application or injection directly for fat treatment without the need for surgical intervention.

11 Claims, 7 Drawing Sheets

METHODS OF ADIPOLYSIS AND COMPOSITIONS USEFUL THEREIN

CROSS-REFERENCE TO RELATED APPLICATIONS

This application claims priority under 35 U.S.C. § 119(e) to U.S. Provisional Application Ser. No. 62/236,037, filed Oct. 1, 2015, the entirety of which is incorporated herein by reference.

FIELD

The present invention is related to compositions and methods useful for the non-surgical treatment of subcutaneous fat, or a localized fat accumulation. Specifically, the present invention is related to pharmacologically active compositions that are suitable for topical application or injection directly into fat without the need for surgical intervention.

BACKGROUND

Concerns over body image, specifically fat, have often been a reason for image conscious individuals to seek various treatments for the treatment of fat. Such treatments include surgical options (such as liposuction, which basically "vacuums" fat out of the body via one or more incisions), "nonsurgical procedures", including COOLSCULPTING® (which appears to cause reperfusion injury to subcutaneous fat, and consequent adipocyte death), and injections of various chemical, not all of which are approved for such treatment—one such example of an approved treatment is KYBELLA® in the US, a first in class drug, which is injectable deoxycholic acid that causes adipolysis in situ via an injection of the drug. Some companies are exploring other injectable therapies—other unapproved injections such as ESSENTIALE® and LIPOSTABIL® do exist.

However, surgical and device related procedures, including liposuction, lipoplasty or suction lipectomy involve the surgical removal of fat deposits using suction, optionally assisted by certain solutions to facilitate fat removal. Liposuction removes fat through an incision in the skin and fat is aspirated by suction through a cannula while the patient is under some sort of anesthesia.

Sometimes liposuction uses fluid injection methodologies wherein a medicated solution containing a mixture of salts, anesthetics and vasoconstrictors or other actives are infused into the treatment site. Examples of adjuvant solutions for liposuction are found in U.S. Pat. No. 5,891,083 ('083). For example, '083 discloses an enzyme, such as a lipase or colipase, added to a carrier. In every embodiment of '083, the solution is administered prior to liposuction. Nowhere in '083 is the use of such a solution alone disclosed as a non-surgical means for removing fat from the body.

Liposuction and device-related methods of fat removal are associated with significant adverse events including temporary bruising, swelling, numbness, soreness and burning sensation, risk of infection, pigmentation changes, the formation of fat clots or blood clots, excessive fluid loss (which can lead to shock) or fluid accumulation that must be drained, friction burns (or other damage to the skin or nerves), or perforation injury to the vital organs. Additionally, such methods often require a recovery time of one to two weeks wherein the patient cannot perform certain daily activities. Moreover, because surgical procedures such as liposuction require local and occasionally general anesthesia, significant anesthesia-related risks are associated with surgical fat removal.

Therefore, it would be desirable to have a method of removing localized fat accumulations that does not require surgery or prolonged recovery time and has fewer adverse side effects than currently available methods.

In each of these procedures, surgical and non-surgical, the attendant risks of such treatments are apparent, thus there has been a desire to provide a less invasive method of treatment. For example, Topokine Therapeutics is exploring a non-invasive topical treatment referred to as XAF5 OINTMENT. While such research continues, the need for a safe and effective non-invasive composition to treat subcutaneous fat remains.

SUMMARY

Provided herein, in one aspect, are methods of reducing subcutaneous fat in a subject in need thereof, the method comprising administering to the subject a topical or injectable composition comprising a statin. In some embodiments, the statin is selected from the group consisting of lovastatin, simvastatin, and fluvastatin. In some embodiments, the statin is lovastatin. In some embodiments, the statin is simvastatin. In some embodiments, the statin is fluvastatin. In some embodiments, the method excludes surgical intervention. In some embodiments, the topical or injectable composition further comprises one or more additional active compounds. In some embodiments, the one or more additional active compounds are selected from anti-inflammatory agents, analgesics, and dispersion agents. In some embodiments, the topical or injectable composition further comprises one or more pharmaceutically acceptable and/or cosmetically acceptable excipients. In some embodiments, the subcutaneous fat is located on the abdomen, chest, back, breast, buttocks, hips, thighs, legs, knees, arms, chin, neck, or face. In some embodiments, the subject suffers from obesity, excess fat on the breast, gynecomastia, drug-induced obesity, hypothyroidism, pseudohypoparathyroidism, hypothalamic obesity, polycystic ovarian disease, depression, binge eating, postpartum obesity, obesity associated with smoking cessation, Prader-Willi syndrome, Bardet-Biedl syndrome, Cohen syndrome, Down syndrome, Turner syndrome, growth hormone deficiency, growth hormone resistance, leptin deficiency or resistance, Cushing syndrome, pseudo-Cushing syndrome, hypertrophy of dorsocervical fat/dorsocervical fat hypertrophy ("buffalo hump"), moon facies, lipoma, or excess fat on the chin.

Provided herein, in another aspect, are topical compositions comprising one or more pharmaceutically acceptable and/or cosmetically acceptable excipients and a statin. In some embodiments, the statin is selected from the group consisting of lovastatin, simvastatin, and fluvastatin. In some embodiments, the statin is lovastatin. In some embodiments, the statin is simvastatin. In some embodiments, the statin is fluvastatin. In some embodiments, the excipients comprise transcutol, ethanol, or a combination thereof.

Provided herein, in another aspect, are injectable compositions comprising one or more pharmaceutically acceptable and/or cosmetically acceptable excipients and a statin. In some embodiments, the statin is selected from the group consisting of lovastatin, simvastatin, and fluvastatin. In some embodiments, the statin is lovastatin. In some embodiments, the statin is simvastatin. In some embodiments, the statin is fluvastatin. In some embodiments, the composition further comprises one or more additional active compounds.

In some embodiments, the one or more additional active compounds are selected from anti-inflammatory agents, analgesics, and dispersion agents.

Provided herein, in another aspect, are methods for the non-surgical removal of localized fat deposits in a subject having localized fat accumulation, the method comprising administering to the subject a fat reducing amount of a composition comprising a statin, wherein the non-surgical method does not include liposuction. In some embodiments, the statin is selected from the group consisting of lovastatin, simvastatin, and fluvastatin. In some embodiments, the statin is lovastatin. In some embodiments, the statin is simvastatin. In some embodiments, the statin is fluvastatin. In some embodiments, the administering step is by topical administration or by injection. In some embodiments, the composition further comprises one or more additional active compounds. In some embodiments, the one or more additional active compounds are selected from anti-inflammatory agents, analgesics, and dispersion agents. In some embodiments, the composition further comprises one or more pharmaceutically acceptable and/or cosmetically acceptable excipients. In some embodiments, the localized fat deposits are located on the abdomen, chest, back, breast, buttocks, hips, thighs, legs, knees, arms, chin, neck, or face. In some embodiments, the subject suffers from obesity, excess fat on the breast, gynecomastia, drug-induced obesity, hypothyroidism, pseudohypoparathyroidism, hypothalamic obesity, polycystic ovarian disease, depression, binge eating, postpartum obesity, obesity associated with smoking cessation, Prader-Willi syndrome, Bardet-Biedl syndrome, Cohen syndrome, Down syndrome, Turner syndrome, growth hormone deficiency, growth hormone resistance, leptin deficiency or resistance, Cushing syndrome, pseudo-Cushing syndrome, hypertrophy of dorsocervical fat/dorsocervical fat hypertrophy ("buffalo hump"), moon facies, lipoma, or excess fat on the chin.

Provided herein, in another aspect, are methods for the removal of localized accumulation of fat in a subject with lower eyelid fat herniation, the method comprising administering to the subject a fat reducing amount of a composition comprising a statin. In some embodiments, the statin is selected from the group consisting of lovastatin, simvastatin, and fluvastatin. In some embodiments, the statin is lovastatin. In some embodiments, the statin is simvastatin. In some embodiments, the statin is fluvastatin. In some embodiments, the administering step is by topical administration or by injection. In some embodiments, the composition further comprises one or more additional active compounds. In some embodiments, the one or more additional active compounds are selected from anti-inflammatory agents, analgesics, and dispersion agents. In some embodiments, the composition further comprises one or more pharmaceutically acceptable and/or cosmetically acceptable excipients. In some embodiments, the method excludes surgical intervention.

Provided herein, in another aspect, are uses of a topical or injectable composition comprising a statin in a method of reducing subcutaneous fat in a subject in need thereof by administering the statin to a subject in need thereof. In some embodiments, the statin is selected from the group consisting of lovastatin, simvastatin, and fluvastatin. In some embodiments, the statin is lovastatin. In some embodiments, the statin is simvastatin. In some embodiments, the statin is fluvastatin. In some embodiments, the use excludes surgical intervention. In some embodiments, the topical or injectable composition further comprises one or more additional active compounds. In some embodiments, the one or more additional active compounds are selected from anti-inflammatory agents, analgesics, and dispersion agents. In some embodiments, the topical or injectable composition further comprises one or more pharmaceutically acceptable and/or cosmetically acceptable excipients. In some embodiments, the subcutaneous fat is located on the abdomen, chest, back, breast, buttocks, hips, thighs, legs, knees, arms, chin, neck, or face. In some embodiments, the subject suffers from obesity, excess fat on the breast, gynecomastia, drug-induced obesity, hypothyroidism, pseudohypoparathyroidism, hypothalamic obesity, polycystic ovarian disease, depression, binge eating, postpartum obesity, obesity associated with smoking cessation, Prader-Willi syndrome, Bardet-Biedl syndrome, Cohen syndrome, Down syndrome, Turner syndrome, growth hormone deficiency, growth hormone resistance, leptin deficiency or resistance, Cushing syndrome, pseudo-Cushing syndrome, hypertrophy of dorsocervical fat/dorsocervical fat hypertrophy ("buffalo hump"), moon facies, lipoma, or excess fat on the chin.

Provided herein, in another aspect, are uses of a fat reducing amount of a composition comprising a statin in a non-surgical method for the removal of localized fat deposits in a subject having localized fat accumulation, by administering to the subject a fat reducing amount of the statin, wherein the non-surgical method does not include liposuction. In some embodiments, the statin is selected from the group consisting of lovastatin, simvastatin, and fluvastatin. In some embodiments, the statin is lovastatin. In some embodiments, the statin is simvastatin. In some embodiments, the statin is fluvastatin. In some embodiments, the administration comprises topical administration or by injection. In some embodiments, the composition further comprises one or more additional active compounds. In some embodiments, the one or more additional active compounds are selected from anti-inflammatory agents, analgesics, and dispersion agents. In some embodiments, the composition further comprises one or more pharmaceutically acceptable and/or cosmetically acceptable excipients. In some embodiments, the localized fat deposits are located on the abdomen, chest, back, breast, buttocks, hips, thighs, legs, knees, arms, chin, neck, or face. In some embodiments, the subject suffers from obesity, excess fat on the breast, gynecomastia, drug-induced obesity, hypothyroidism, pseudohypoparathyroidism, hypothalamic obesity, polycystic ovarian disease, depression, binge eating, postpartum obesity, obesity associated with smoking cessation, Prader-Willi syndrome, Bardet-Biedl syndrome, Cohen syndrome, Down syndrome, Turner syndrome, growth hormone deficiency, growth hormone resistance, leptin deficiency or resistance, Cushing syndrome, pseudo-Cushing syndrome, hypertrophy of dorsocervical fat/dorsocervical fat hypertrophy ("buffalo hump"), moon facies, lipoma, or excess fat on the chin.

Provided herein, in another aspect, are uses of a fat reducing amount of a composition comprising a statin in a method for the removal of localized accumulation of fat in a subject with lower eyelid fat herniation by administering to the subject a fat reducing amount of a composition comprising a statin. In some embodiments, the statin is selected from the group consisting of lovastatin, simvastatin, and fluvastatin. In some embodiments, the statin is lovastatin. In some embodiments, the statin is simvastatin. In some embodiments, the statin is fluvastatin. In some embodiments, the administering is by topical administration or by injection. In some embodiments, the composition further comprises one or more additional active compounds. In some embodiments, the one or more additional active compounds are selected from anti-inflammatory agents, analgesics, and dispersion agents. In some embodiments, the composition further comprises one or more pharmaceutically acceptable and/or cosmetically acceptable excipients.

DETAILED DESCRIPTION

Figure 1:
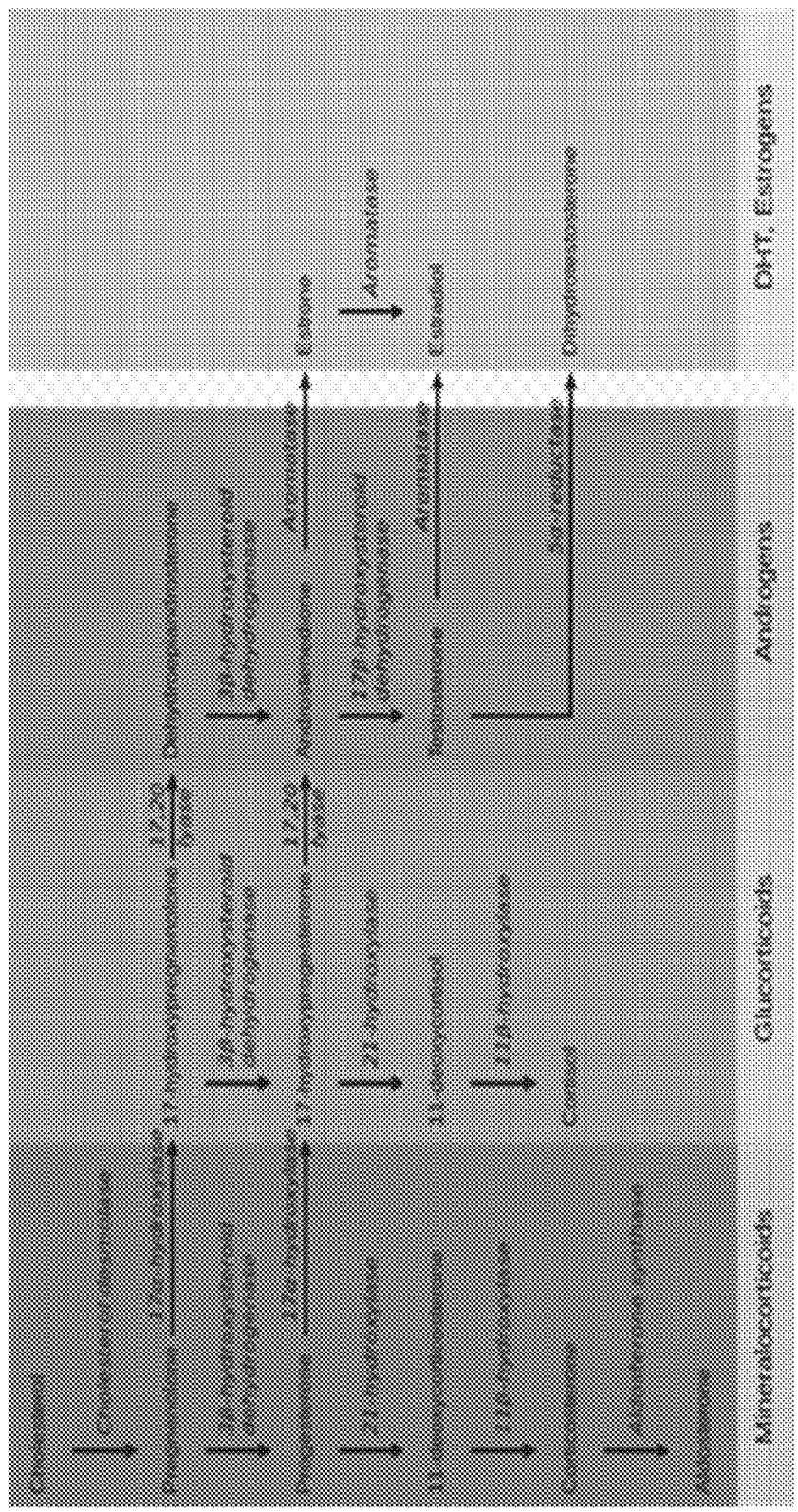
FIG. 1 depicts pregnenolone and non-limiting examples of steroids derived therefrom.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

A "therapeutically effective amount," as used herein, refers to a sufficient amount of a composition of the invention being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case can be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is to be understood that "an effective amount" or "a therapeutically effective amount" can vary from subject to subject, due to variation in metabolism, age, weight, general condition of the subject, the condition being treated, the severity of the condition being treated, and the judgment of the prescribing physician.

As used herein an "adipose tissue-reducing" amount refers to a sufficient amount of the composition of the invention needed to reduce adipose tissue. It is to be understood that the amount sufficient to decrease the adipose tissue will vary from subject to subject due to variation in metabolism, age, weight, general condition of the subject, the severity of the condition being treated, and the judgment of the prescribing physician.

For the purposes of the present invention, a non-surgical method of fat removal does not include liposuction, lipoplasty or suction lipectomy. As used herein, "non-surgical" refers to medical procedures that do not require an incision. Injections are non-limiting examples of non-surgical procedures. In some embodiments, a method described herein excludes surgical intervention.

We have found that subcutaneous fat is reduced or obliterated via topical application or injection of the agents described therein. Histology examination of skin sections shows a reduction in both size and in number of adipocytes. However, it appears that the subcutaneous fat is reduced or disappears. It is unknown whether pre-adipocytes are destroyed or changed in any way.

Accordingly, in one aspect, provided herein are topical or injectable compositions comprising an active agent or active compound described herein. In some embodiments, the compositions are for the reduction or removal of subcutaneous fat in a subject in need thereof. In some embodiments, the compositions are for the reduction or removal of localized fat deposits in a subject in need thereof.

In one embodiment of the present invention, a medical composition for the non-surgical removal of localized fat deposits in a patient is provided which comprises at least one pharmacologically active compound described herein, optionally at least one pharmaceutically acceptable excipient and optionally at least one additional active ingredient. In some embodiments, a cosmetic composition for the non-surgical removal of localized fat deposits in a subject is provided which comprises at least one active compound described herein, optionally at least one cosmetically acceptable excipient and optionally at least one additional active ingredient.

In some embodiments, the composition for the non-surgical removal of localized fat deposits in a subject comprises, consists essentially of, or consists of at least one active compound selected from a statin, an alpha/beta adrenergic ligand (i.e., an alpha/beta adrenergic receptor ligand), and a steroid; optionally at least one pharmaceutically acceptable and/or cosmetically acceptable excipient; and optionally at least one additional active ingredient. In some embodiments, the composition for the non-surgical removal of localized fat deposits in a subject comprises, consists essentially of, or consists of at least one active compound selected from a statin, an alpha/beta adrenergic ligand, and a steroid; and at least one pharmaceutically acceptable and/or cosmetically acceptable excipient. In some embodiments, the composition for the non-surgical removal of localized fat deposits in a subject comprises, consists essentially of, or consists of a statin; and at least one pharmaceutically acceptable and/or cosmetically acceptable excipient. In some embodiments, the composition for the non-surgical removal of localized fat deposits in a subject comprises, consists essentially of, or consists of an alpha/beta adrenergic ligand; and at least one pharmaceutically acceptable and/or cosmetically acceptable excipient. In some embodiments, the composition for the non-surgical removal of localized fat deposits in a subject comprises, consists essentially of, or consists of a steroid; and at least one pharmaceutically acceptable and/or cosmetically acceptable excipient.

In another embodiment of the present invention, a medical composition is provided for removing localized accumulation of fat in a patient with lower eyelid fat herniation comprising a fat reducing amount of the active described herein. In some embodiments, a medical composition is provided for removing localized accumulation of fat in a patient with lower eyelid fat herniation comprising a fat reducing amount of a statin.

In another aspect, provided herein are methods of reducing subcutaneous fat in a subject in need thereof, the method comprising administering to the subject a topical or injectable composition described herein. In some embodiments, the method comprises administering to the subject a topical or injectable composition comprising, consisting essentially of, or consisting of at least one active compound selected from a statin, an alpha/beta adrenergic ligand, and a steroid; and at least one pharmaceutically acceptable and/or cosmetically acceptable excipient. In some embodiments, the method comprises administering to the subject a topical or injectable composition comprising, consisting essentially of, or consisting of a statin; and at least one pharmaceutically acceptable and/or cosmetically acceptable excipient.

In some embodiments, provided herein are methods of reducing subcutaneous fat in a subject in need thereof, the method comprising administering to the subject an injectable composition comprising a statin and at least one pharmaceutically acceptable excipient. In some embodiments, provided herein are methods of reducing subcutaneous fat in a subject in need thereof, the method comprising administering to the subject an injectable composition consisting essentially of a statin and at least one pharmaceutically acceptable excipient.

In some embodiments, provided herein are methods of reducing subcutaneous fat in a subject in need thereof, the method comprising administering to the subject an injectable composition comprising a statin and at least one pharmaceutically acceptable excipient, wherein the composition is locally injected at the abdomen, chest, back, breast, buttocks, hips, thighs, legs, knees, arms, chin, neck and/or face. In some embodiments, provided herein are methods of reducing subcutaneous fat in a subject in need thereof, the method comprising administering to the subject an injectable composition consisting essentially of a statin and at least one pharmaceutically acceptable excipient, wherein the composition is locally injected at the abdomen, chest, back, breast, buttocks, hips, thighs, legs, knees, arms, chin, neck and/or face.

In some embodiments, provided herein are methods of reducing subcutaneous fat in a subject in need thereof, the method comprising administering to the subject an injectable composition comprising a statin and at least one pharmaceutically acceptable excipient, wherein the composition is locally injected as a plurality of injections (i.e., two or more injections) at the abdomen, chest, back, breast, buttocks, hips, thighs, legs, knees, arms, chin, neck and/or face. In some embodiments, provided herein are methods of reducing subcutaneous fat in a subject in need thereof, the method comprising administering to the subject an injectable composition consisting essentially of a statin and at least one pharmaceutically acceptable excipient, wherein the composition is locally injected as a plurality of injections at the abdomen, chest, back, breast, buttocks, hips, thighs, legs, knees, arms, chin, neck and/or face.

In some embodiments, provided herein are methods of reducing subcutaneous fat in a subject in need thereof, the method comprising administering to the subject an injectable composition comprising a statin and at least one pharmaceutically acceptable excipient, wherein the composition is locally injected one more times at the abdomen, chest, back, breast, buttocks, hips, thighs, legs, knees, arms, chin, neck and/or face. In some embodiments, provided herein are methods of reducing subcutaneous fat in a subject in need thereof, the method comprising administering to the subject an injectable composition consisting essentially of a statin and at least one pharmaceutically acceptable excipient, wherein the composition is locally injected one more times at the abdomen, chest, back, breast, buttocks, hips, thighs, legs, knees, arms, chin, neck and/or face.

In some embodiments, provided herein are methods of reducing subcutaneous fat in a subject in need thereof, the method comprising administering to the subject an injectable composition comprising a statin and at least one pharmaceutically acceptable excipient, wherein the composition is locally injected one more times at the abdomen, chest, back, breast, buttocks, hips, thighs, legs, knees, arms, chin, neck and/or face, each injection spaced at least one centimeter apart from one another. In some embodiments, provided herein are methods of reducing subcutaneous fat in a subject in need thereof, the method comprising administering to the subject an injectable composition consisting essentially of a statin and at least one pharmaceutically acceptable excipient, wherein the composition is locally injected one more times at the abdomen, chest, back, breast, buttocks, hips, thighs, legs, knees, arms, chin, neck and/or face, each injection spaced at least one centimeter apart from one another.

In some embodiments, provided herein are methods of reducing subcutaneous fat in a subject in need thereof, the method comprising administering to the subject an injectable composition comprising a statin and at least one cosmetically acceptable excipient. In some embodiments, provided herein are methods of reducing subcutaneous fat in a subject in need thereof, the method comprising administering to the subject an injectable composition consisting essentially of a statin and at least one cosmetically acceptable excipient.

In some embodiments, provided herein are methods of reducing subcutaneous fat in a subject in need thereof, the method comprising administering to the subject an injectable composition comprising a statin and at least one cosmetically acceptable excipient, wherein the composition is locally injected at the abdomen, chest, back, breast, buttocks, hips, thighs, legs, knees, arms, chin, neck and/or face. In some embodiments, provided herein are methods of reducing subcutaneous fat in a subject in need thereof, the method comprising administering to the subject an injectable composition consisting essentially of a statin and at least one cosmetically acceptable excipient, wherein the composition is locally injected at the abdomen, chest, back, breast, buttocks, hips, thighs, legs, knees, arms, chin, neck and/or face.

In some embodiments, provided herein are methods of reducing subcutaneous fat in a subject in need thereof, the method comprising administering to the subject an injectable composition comprising a statin and at least one cosmetically acceptable excipient, wherein the composition is locally injected as a plurality of injections (i.e., two or more injections) at the abdomen, chest, back, breast, buttocks, hips, thighs, legs, knees, arms, chin, neck and/or face. In some embodiments, provided herein are methods of reducing subcutaneous fat in a subject in need thereof, the method comprising administering to the subject an injectable composition consisting essentially of a statin and at least one cosmetically acceptable excipient, wherein the composition is locally injected as a plurality of injections at the abdomen, chest, back, breast, buttocks, hips, thighs, legs, knees, arms, chin, neck and/or face.

In some embodiments, provided herein are methods of reducing subcutaneous fat in a subject in need thereof, the method comprising administering to the subject an injectable composition comprising a statin and at least one cosmetically acceptable excipient, wherein the composition is locally injected one more times at the abdomen, chest, back, breast, buttocks, hips, thighs, legs, knees, arms, chin, neck and/or face. In some embodiments, provided herein are methods of reducing subcutaneous fat in a subject in need thereof, the method comprising administering to the subject an injectable composition consisting essentially of a statin and at least one cosmetically acceptable excipient, wherein the composition is locally injected one more times at the abdomen, chest, back, breast, buttocks, hips, thighs, legs, knees, arms, chin, neck and/or face.

In some embodiments, provided herein are methods of reducing subcutaneous fat in a subject in need thereof, the method comprising administering to the subject an injectable composition comprising a statin and at least one cosmetically acceptable excipient, wherein the composition is locally injected one more times at the abdomen, chest, back, breast, buttocks, hips, thighs, legs, knees, arms, chin, neck and/or face, each injection spaced at least one centimeter apart from one another. In some embodiments, provided herein are methods of reducing subcutaneous fat in a subject in need thereof, the method comprising administering to the subject an injectable composition consisting essentially of a statin and at least one cosmetically acceptable excipient, wherein the composition is locally injected one more times at the abdomen, chest, back, breast, buttocks, hips, thighs, legs, knees, arms, chin, neck and/or face, each injection spaced at least one centimeter apart from one another.

In another embodiment of the present invention, a method is provided for the non-surgical removal of localized fat deposits in a patient having localized fat accumulation comprising administering a fat reducing amount of a composition, wherein the non-surgical method does not include liposuction. In some embodiments, a non-surgical method is provided for the removal of localized fat deposits in a subject having localized fat accumulation comprising administering to the subject a composition comprising, consisting essentially of, or consisting of a fat reducing amount of an active compound described herein. In some embodiments, a non-surgical method is provided for the removal of localized fat deposits in a subject having localized fat accumulation comprising administering to the subject a composition comprising, consisting essentially of, or consisting of a fat reducing amount of a statin and at least one pharmaceutically acceptable and/or cosmetically acceptable excipient.

In some embodiments, provided herein are methods of reducing subcutaneous fat in a subject in need thereof, the method comprising administering to the subject a topical composition comprising a statin and at least one pharmaceutically acceptable excipient. In some embodiments, provided herein are methods of reducing subcutaneous fat in a subject in need thereof, the method comprising administering to the subject a topical composition consisting essentially of a statin and at least one pharmaceutically acceptable excipient.

In some embodiments, provided herein are methods of reducing subcutaneous fat in a subject in need thereof, the method comprising administering to the subject a topical composition comprising a statin and at least one pharmaceutically acceptable excipient, wherein the composition is administered at the abdomen, chest, back, breast, buttocks, hips, thighs, legs, knees, arms, chin, neck and/or face. In some embodiments, provided herein are methods of reducing subcutaneous fat in a subject in need thereof, the method comprising administering to the subject a topical composition consisting essentially of a statin and at least one pharmaceutically acceptable excipient, wherein the composition is administered at the abdomen, chest, back, breast, buttocks, hips, thighs, legs, knees, arms, chin, neck and/or face.

In some embodiments, provided herein are methods of reducing subcutaneous fat in a subject in need thereof, the method comprising administering to the subject a topical composition comprising a statin and at least one cosmetically acceptable excipient. In some embodiments, provided herein are methods of reducing subcutaneous fat in a subject in need thereof, the method comprising administering to the subject a topical composition consisting essentially of a statin and at least one cosmetically acceptable excipient.

In some embodiments, provided herein are methods of reducing subcutaneous fat in a subject in need thereof, the method comprising administering to the subject a topical composition comprising a statin and at least one cosmetically acceptable excipient, wherein the composition is administered at the abdomen, chest, back, breast, buttocks, hips, thighs, legs, knees, arms, chin, neck and/or face. In some embodiments, provided herein are methods of reducing subcutaneous fat in a subject in need thereof, the method comprising administering to the subject a topical composition consisting essentially of a statin and at least one cosmetically acceptable excipient, wherein the composition is administered at the abdomen, chest, back, breast, buttocks, hips, thighs, legs, knees, arms, chin, neck and/or face.

In another embodiment of the present invention, a method is provided for the non-surgical removal of localized fat deposits in a patient having localized fat accumulation comprising administering a fat reducing amount of a composition, wherein the non-surgical method does not include liposuction. In some embodiments, a non-surgical method is provided for the removal of localized fat deposits in a subject having localized fat accumulation comprising administering to the subject a composition comprising, consisting essentially of, or consisting of a fat reducing amount of an active compound described herein. In some embodiments, a non-surgical method is provided for the removal of localized fat deposits in a subject having localized fat accumulation comprising administering to the subject a composition comprising, consisting essentially of, or consisting of a fat reducing amount of a statin and at least one pharmaceutically acceptable or cosmetically acceptable excipient.

In some embodiments, provided herein are non-surgical methods for the removal of localized fat deposits in a subject having localized fat accumulation comprising administering to the subject a composition comprising a fat reducing amount of a statin and at least one pharmaceutically acceptable excipient. In some embodiments, provided herein are non-surgical methods for the removal of localized fat deposits in a subject having localized fat accumulation comprising administering to the subject a composition consisting essentially of a fat reducing amount of a statin and at least one pharmaceutically acceptable excipient.

In some embodiments, provided herein are non-surgical methods for the removal of localized fat deposits in a subject having localized fat accumulation comprising administering to the subject an injectable composition comprising a fat reducing amount of a statin and at least one pharmaceutically acceptable excipient. In some embodiments, provided herein are non-surgical methods for the removal of localized fat deposits in a subject having localized fat accumulation comprising administering to the subject an injectable composition consisting essentially of a fat reducing amount of a statin and at least one pharmaceutically acceptable excipient.

In some embodiments, provided herein are non-surgical methods for the removal of localized fat deposits in a subject having localized fat accumulation comprising administering to the subject an injectable composition comprising a fat reducing amount of a statin and at least one pharmaceutically acceptable excipient, wherein the composition is locally injected at the abdomen, chest, back, breast, buttocks, hips, thighs, legs, knees, arms, chin, neck and/or face. In some embodiments, provided herein are non-surgical methods for the removal of localized fat deposits in a subject having localized fat accumulation comprising administering to the subject an injectable composition consisting essentially of a fat reducing amount of a statin and at least one pharmaceutically acceptable excipient, wherein the composition is locally injected at the abdomen, chest, back, breast, buttocks, hips, thighs, legs, knees, arms, chin, neck and/or face.

In some embodiments, provided herein are non-surgical methods for the removal of localized fat deposits in a subject having localized fat accumulation comprising administering to the subject an injectable composition comprising a fat reducing amount of a statin and at least one pharmaceutically acceptable excipient, wherein the composition is locally injected one more times at the abdomen, chest, back, breast, buttocks, hips, thighs, legs, knees, arms, chin, neck and/or face. In some embodiments, provided herein are non-surgical methods for the removal of localized fat deposits in a subject having localized fat accumulation comprising administering to the subject an injectable composition consisting essentially of a fat reducing amount of a statin and at least one pharmaceutically acceptable excipient, wherein the composition is locally injected one more times at the abdomen, chest, back, breast, buttocks, hips, thighs, legs, knees, arms, chin, neck and/or face.

In some embodiments, provided herein are non-surgical methods for the removal of localized fat deposits in a subject having localized fat accumulation comprising administering to the subject an injectable composition comprising a fat reducing amount of a statin and at least one pharmaceutically acceptable excipient, wherein the composition is locally injected one more times at the abdomen, chest, back, breast, buttocks, hips, thighs, legs, knees, arms, chin, neck and/or face, each injection spaced at least one centimeter apart from one another. In some embodiments, provided herein are non-surgical methods for the removal of localized fat deposits in a subject having localized fat accumulation comprising administering to the subject an injectable composition consisting essentially of a fat reducing amount of a statin and at least one pharmaceutically acceptable excipient, wherein the composition is locally injected one more times at the abdomen, chest, back, breast, buttocks, hips, thighs, legs, knees, arms, chin, neck and/or face, each injection spaced at least one centimeter apart from one another.

In some embodiments, provided herein are non-surgical methods for the removal of localized fat deposits in a subject having localized fat accumulation comprising administering to the subject a composition comprising a fat reducing amount of a statin and at least one cosmetically acceptable excipient. In some embodiments, provided herein are non-surgical methods for the removal of localized fat deposits in a subject having localized fat accumulation comprising administering to the subject a composition consisting essentially of a fat reducing amount of a statin and at least one cosmetically acceptable excipient.

In some embodiments, provided herein are non-surgical methods for the removal of localized fat deposits in a subject having localized fat accumulation comprising administering to the subject an injectable composition comprising a fat reducing amount of a statin and at least one cosmetically acceptable excipient. In some embodiments, provided herein are non-surgical methods for the removal of localized fat deposits in a subject having localized fat accumulation comprising administering to the subject an injectable composition consisting essentially of a fat reducing amount of a statin and at least one cosmetically acceptable excipient.

In some embodiments, provided herein are non-surgical methods for the removal of localized fat deposits in a subject having localized fat accumulation comprising administering to the subject an injectable composition comprising a fat reducing amount of a statin and at least one cosmetically acceptable excipient, wherein the composition is locally injected at the abdomen, chest, back, breast, buttocks, hips, thighs, legs, knees, arms, chin, neck and/or face. In some embodiments, provided herein are non-surgical methods for the removal of localized fat deposits in a subject having localized fat accumulation comprising administering to the subject an injectable composition consisting essentially of a fat reducing amount of a statin and at least one cosmetically acceptable excipient, wherein the composition is locally injected at the abdomen, chest, back, breast, buttocks, hips, thighs, legs, knees, arms, chin, neck and/or face.

In some embodiments, provided herein are non-surgical methods for the removal of localized fat deposits in a subject having localized fat accumulation comprising administering to the subject an injectable composition comprising a fat reducing amount of a statin and at least one cosmetically acceptable excipient, wherein the composition is locally injected one more times at the abdomen, chest, back, breast, buttocks, hips, thighs, legs, knees, arms, chin, neck and/or face. In some embodiments, provided herein are non-surgical methods for the removal of localized fat deposits in a subject having localized fat accumulation comprising administering to the subject an injectable composition consisting essentially of a fat reducing amount of a statin and at least one cosmetically acceptable excipient, wherein the composition is locally injected one more times at the abdomen, chest, back, breast, buttocks, hips, thighs, legs, knees, arms, chin, neck and/or face.

In some embodiments, provided herein are non-surgical methods for the removal of localized fat deposits in a subject having localized fat accumulation comprising administering to the subject an injectable composition comprising a fat reducing amount of a statin and at least one cosmetically acceptable excipient, wherein the composition is locally injected one more times at the abdomen, chest, back, breast, buttocks, hips, thighs, legs, knees, arms, chin, neck and/or face, each injection spaced at least one centimeter apart from one another. In some embodiments, provided herein are non-surgical methods for the removal of localized fat deposits in a subject having localized fat accumulation comprising administering to the subject an injectable composition consisting essentially of a fat reducing amount of a statin and at least one cosmetically acceptable excipient, wherein the composition is locally injected one more times at the abdomen, chest, back, breast, buttocks, hips, thighs, legs, knees, arms, chin, neck and/or face, each injection spaced at least one centimeter apart from one another.

In some embodiments, provided herein are non-surgical methods for the removal of localized fat deposits in a subject having localized fat accumulation comprising administering to the subject a topical composition comprising a fat reducing amount of a statin and at least one pharmaceutically acceptable excipient. In some embodiments, provided herein are non-surgical methods for the removal of localized fat deposits in a subject having localized fat accumulation comprising administering to the subject a topical composition consisting essentially of a fat reducing amount of a statin and at least one pharmaceutically acceptable excipient.

In some embodiments, provided herein are non-surgical methods for the removal of localized fat deposits in a subject having localized fat accumulation comprising administering to the subject a topical composition comprising a fat reducing amount of a statin and at least one pharmaceutically acceptable excipient, wherein the composition is administered at the abdomen, chest, back, breast, buttocks, hips, thighs, legs, knees, arms, chin, neck and/or face. In some embodiments, provided herein are non-surgical methods for the removal of localized fat deposits in a subject having localized fat accumulation comprising administering to the subject a topical composition consisting essentially of a fat reducing amount of a statin and at least one pharmaceutically acceptable excipient, wherein the composition is administered at the abdomen, chest, back, breast, buttocks, hips, thighs, legs, knees, arms, chin, neck and/or face.

In some embodiments, provided herein are non-surgical methods for the removal of localized fat deposits in a subject having localized fat accumulation comprising administering to the subject a topical composition comprising a fat reducing amount of a statin and at least one cosmetically acceptable excipient. In some embodiments, provided herein are non-surgical methods for the removal of localized fat deposits in a subject having localized fat accumulation comprising administering to the subject a topical composition consisting essentially of a fat reducing amount of a statin and at least one cosmetically acceptable excipient.

In some embodiments, provided herein are non-surgical methods for the removal of localized fat deposits in a subject having localized fat accumulation comprising administering to the subject a topical composition comprising a fat reducing amount of a statin and at least one cosmetically acceptable excipient, wherein the composition is administered at the abdomen, chest, back, breast, buttocks, hips, thighs, legs, knees, arms, chin, neck and/or face. In some embodiments, provided herein are non-surgical methods for the removal of localized fat deposits in a subject having localized fat accumulation comprising administering to the subject a topical composition consisting essentially of a fat reducing amount of a statin and at least one cosmetically acceptable excipient, wherein the composition is administered at the abdomen, chest, back, breast, buttocks, hips, thighs, legs, knees, arms, chin, neck and/or face.

In some embodiments, a method is provided for the removal of localized accumulation of fat in a subject with lower eyelid fat herniation comprising administration of a composition comprising, consisting essentially of, or consisting of a fat reducing amount of the active described herein. In some embodiments, a method is provided for the removal of localized accumulation of fat in a subject with lower eyelid fat herniation comprising administration of a composition comprising, consisting essentially of, or consisting of a fat reducing amount of a statin and at least one pharmaceutically acceptable and/or cosmetically acceptable excipient.

In some embodiments, provided herein are methods for the removal of localized accumulation of fat in a subject with lower eyelid fat herniation comprising administering to the subject a composition comprising a fat reducing amount of a statin and at least one pharmaceutically acceptable excipient. In some embodiments, provided herein are methods for the removal of localized accumulation of fat in a subject with lower eyelid fat herniation comprising administering to the subject a composition consisting essentially of a fat reducing amount of a statin and at least one pharmaceutically acceptable excipient.

In some embodiments, provided herein are methods for the removal of localized accumulation of fat in a subject with lower eyelid fat herniation comprising administering to the subject an injectable composition comprising a fat reducing amount of a statin and at least one pharmaceutically acceptable excipient. In some embodiments, provided herein are methods for the removal of localized accumulation of fat in a subject with lower eyelid fat herniation comprising administering to the subject an injectable composition consisting essentially of a fat reducing amount of a statin and at least one pharmaceutically acceptable excipient.

In some embodiments, provided herein are methods for the removal of localized accumulation of fat in a subject with lower eyelid fat herniation comprising administering to the subject a topical composition comprising a fat reducing amount of a statin and at least one pharmaceutically acceptable excipient. In some embodiments, provided herein are methods for the removal of localized accumulation of fat in a subject with lower eyelid fat herniation comprising administering to the subject a topical composition consisting essentially of a fat reducing amount of a statin and at least one pharmaceutically acceptable excipient.

In some embodiments, provided herein are methods for the removal of localized accumulation of fat in a subject with lower eyelid fat herniation comprising administering to the subject a composition comprising a fat reducing amount of a statin and at least one cosmetically acceptable excipient. In some embodiments, provided herein are methods for the removal of localized accumulation of fat in a subject with lower eyelid fat herniation comprising administering to the subject a composition consisting essentially of a fat reducing amount of a statin and at least one cosmetically acceptable excipient.

In some embodiments, provided herein are methods for the removal of localized accumulation of fat in a subject with lower eyelid fat herniation comprising administering to the subject an injectable composition comprising a fat reducing amount of a statin and at least one cosmetically acceptable excipient. In some embodiments, provided herein are methods for the removal of localized accumulation of fat in a subject with lower eyelid fat herniation comprising administering to the subject an injectable composition consisting essentially of a fat reducing amount of a statin and at least one cosmetically acceptable excipient.

In some embodiments, provided herein are methods for the removal of localized accumulation of fat in a subject with lower eyelid fat herniation comprising administering to the subject a topical composition comprising a fat reducing amount of a statin and at least one cosmetically acceptable excipient. In some embodiments, provided herein are methods for the removal of localized accumulation of fat in a subject with lower eyelid fat herniation comprising administering to the subject a topical composition consisting essentially of a fat reducing amount of a statin and at least one cosmetically acceptable excipient.

The preferred compounds useful in the method and composition of the invention fall into three classes:

alpha/beta adrenergic ligands, for which preferred examples include phentolamine;

statins, for which preferred examples include lovastatin; and steroids, for which preferred examples include pregnenolone, and steroids derived therefrom, more preferable naturally derived therefrom. For example, those compounds, pregnenolone, and steroids derived therefrom are illustrated in FIG. 1.

As used herein, unless otherwise described, the terms "alpha/beta adrenergic ligand," "statin," and "steroid", including their plural forms, encompass the neutral form of the compound, as well as their pharmaceutically acceptable salt, hydrate, solvate, stereoisomer, polymorph, tautomer, or isotopically enriched derivative thereof.

In some embodiments, the active compound is an alpha/beta adrenergic ligand. In some embodiments the active compound is a statin. In some embodiments the active compound is a steroid.

Illustrative statins, include, but are not limited to, atorvastatin, cerivastatin, fluvastatin, lovastatin, mevastatin, pitavastatin, pravastatin, rosuvastatin, and simvastatin. In some embodiments, the statin is a type I statin. Illustrative type I statins include, but are not limited to, lovastatin, pravastatin, and simvastatin. In some embodiments, the statin is a type II statin. Illustrative type II statins include, but are not limited to, fluvastatin, cerivastatin, atorvastatin, and rosuvastatin. In some embodiments, the statin is selected from lovastatin, simvastatin, fluvastatin, rosuvastatin, and atorvastatin. In some embodiments, the statin is selected from lovastatin, simvastatin, and fluvastatin. In some embodiments, the statin is lovastatin. In some embodiments, the statin is simvastatin. In some embodiments, the statin is fluvastatin. In some embodiments, the statin is rosuvastatin. In some embodiments, the statin is atorvastatin. In some embodiments, the statin cannot be rosuvastatin or atorvastatin.

In some embodiments, the alpha/beta adrenergic ligand is an alpha adrenergic ligand. In some embodiments, the alpha/beta adrenergic ligand is a non-selective alpha adrenergic ligand.

In some embodiments, the steroid is a fat cell-lytic steroid. In some embodiments, the fat cell-lytic steroid is pregnenolone or a derivative therefrom. In some embodiments, the steroid is a fat-reducing steroid. In some embodiments, the fat-reducing steroid is pregnenolone or a derivative therefrom.

Most preferred actives include lovastatin, pregnenolone and phentolamine.

Each of the actives described here is useful alone or in combination.

In some embodiments, a concentration of the one or more active agents in the composition is at least 9.75%, 9.50%, 9.25% 9%, 8.75%, 8.50%, 8.25%, 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v, including increments thereof, and subvalues and subranges encompassed within the listed range of values.

In some embodiments, a concentration of the one or more active agents in the composition is less than 10%, 9.75%, 9.50%, 9.25% 9%, 8.75%, 8.50%, 8.25%, 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v, including increments thereof, and subvalues and subranges encompassed within the listed range of values.

In some embodiments, a concentration of the one or more active agents in the composition is about 10%, 9.75%, 9.50%, 9.25% 9%, 8.75%, 8.50%, 8.25%, 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v, including increments thereof, and subvalues and subranges encompassed within the listed range of values. In some embodiments, a concentration of the statin in the composition is about 10%, 9.75%, 9.50%, 9.25% 9%, 8.75%, 8.50%, 8.25%, 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v, including increments thereof, and subvalues and subranges encompassed within the listed range of values.

In some embodiments, a concentration of the one or more active agents in a composition is in the range from approximately 0.01% to approximately 10%, approximately 0.01% to approximately 1%, approximately 0.02% to approximately 10%, approximately 0.02% to approximately 1%, approximately 0.03% to approximately 10%, approximately 0.03% to approximately 1%, approximately 0.04% to approximately 10%, approximately 0.04% to approximately 1%, approximately 0.05% to approximately 10%, approximately 0.05% to approximately 5%, approximately 0.05% to approximately 1%, approximately 0.06% to approximately 10%, approximately 0.06% to approximately 5%, approximately 0.06% to approximately 1%, approximately 0.07% to approximately 10%, approximately 0.07% to approximately 5%, approximately 0.07% to approximately 1%, approximately 0.08% to approximately 10%, approximately 0.08% to approximately 5%, approximately 0.08% to approximately 1%, approximately 0.09% to approximately 10%, approximately 0.09% to approximately 5%, approximately 0.09% to approximately 1%, approximately 0.1% to approximately 10%, approximately 0.1% to approximately 5%, approximately 0.1% to approximately 1%, w/v or v/v, including increments thereof, and subvalues and subranges encompassed within the listed ranges of values.

In some embodiments, a concentration of the one or more active agents in the composition is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10 mM, including increments therein, and subvalues and subranges encompassed within the listed range of values. In some embodiments, a concentration of the statin in the composition is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5 or 20 mM, including increments therein, and subvalues and subranges encompassed within the listed range of values.

In some embodiments, a concentration of the one or more active agents in the composition is, from about 1 mM to about 6 mM, from about 0.1 mM to about 8 mM, or from about 0.5 mM to about 10 mM, including any subranges therein. In some embodiments, a concentration of the statin in the composition is, from about 1 mM to about 6 mM, from about 0.5 mM to about 8 mM, or from about 0.1 mM to about 10 mM, including any sub value and subranges therein.

It is understood that the final concentration is dependent on many factors known to persons skilled in the art including, but not limited to, location and size of the target site.

In some embodiments, a composition herein comprises, consists essentially of, or consists of less than 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g of the one or more active agents herein, and any subvalues and subranges encompassed within the listed range of values.

In some embodiments, a composition herein comprises, consists essentially of, or consists of more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, or 0.095 g of the one or more active agents herein, and sub values and subranges encompassed within the listed range of values.

In some embodiments, a composition herein comprises, consists essentially of, or consists of about 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, or 0.1 g, including increments therein, and subvalues and subranges encompassed within the listed range of values, of the one or more active agents herein. In some embodiments, a composition herein comprises, consists essentially of, or consists of about 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, or 0.1 g, including increments therein, and subvalues and subranges encompassed within the listed range of values, of the statin.

In some embodiments, a composition herein comprises, consists essentially of, or consists of 0.0001-0.100 g, 0.0001-0.020 g, 0.0001-0.010 g, 0.0005-0.100 g, 0.0005-0.020 g, 0.0005-0.010 g, 0.0005-0.005 g, 0.001-0.100 g, 0.001-0.010 g, or 0.001-0.005 g, of the one or more active agents herein, and subvalues and subranges encompassed within the listed range of values. In some embodiments, a composition herein comprises, consists essentially of, or consists of 0.0001-0.100 g, 0.0001-0.020 g, 0.0001-0.010 g, 0.0005-0.100 g, 0.0005-0.020 g, 0.0005-0.010 g, 0.0005-0.005 g, 0.001-0.100 g, 0.001-0.010 g, or 0.001-0.005 g, and subvalues and subranges encompassed within the listed range of values, of statin.

This invention contemplates a topical or injectable composition, formulated using pharmaceutically acceptable and/or cosmetically acceptable excipients. Pharmaceutically acceptable and/or cosmetically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions and agents can be found, for example, in Remington's Pharmaceutical Sciences, Sixteenth Edition, E. W. Martin (Mack Publishing Co., Easton, Pa., 1980), and Remington: The Science and Practice of Pharmacy, 21$^{st}$ Edition (Lippincott Williams & Wilkins, 2005).

Preferred formulations may include purified water, glycerin, aloe barbadensis (aloe vera gel), sodium hyaluronate, potassium sorbate, methylsulfonylmethane (MSM), caprylic/capric triglyceride, *helianthus annuus* (sunflower) seed oil, *butyrospermum parkii* (shea butter), stearic acid, glyceryl stearate, allantoin, lecithin, phenoxyethanol and caprylyl glycol and sodium bicarbonate. More preferred formulations include ethanol, transcutol, isopropyl myristate and dimethyl isosorbide.

Pharmaceutical or cosmetic compositions described herein can be prepared by any method known in the art of pharmacology. In general, such preparatory methods include the steps of bringing the active ingredient into association with a carrier and/or one or more other accessory ingredients, and then, if necessary and/or desirable, shaping and/or packaging the product into a desired single- or multi-dose unit.

Pharmaceutical or cosmetic compositions can be prepared, packaged, and/or sold in bulk, as a single unit dose, and/or as a plurality of single unit doses. As used herein, a "unit dose" is discrete amount of the pharmaceutical or cosmetic composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

A unit dose may comprise, consist essentially of, or consist of an amount of the one or more active agents as disclosed in the compositions herein. In some embodiments, the compositions described herein are administered as a unit dose. Such unit dose can have, for example, a total volume of less than 500 mL, 400 mL, 300 mL, 200 mL, 100 mL, 90 mL, 80 mL, 70 mL, 60 mL, 50 mL, 40 mL, 30 mL, 20 mL, 10 mL, 9 mL, 8 mL, 7 mL, 6, mL 5 mL, 4 mL, 3 mL, 2 mL, 1 mL, 0.9 mL, 0.8 mL, 0.7 mL, 0.6 mL, 0.5 mL, 0.4 mL, 0.3 mL, 0.2 mL, 0.1 mL, 0.09 mL, 0.08 mL, 0.07 mL, 0.06 mL, 0.05 mL, 0.04 mL, 0.03 mL, 0.02 mL, 0.01 mL, 0.009 mL, 0.008 mL, 0.007 mL, 0.006 mL, 0.005 mL, 0.004 mL, 0.003 mL, 0.002 mL, 0.001 mL, 0.0009 mL, 0.0008 mL, 0.0007 mL, 0.0006 mL, 0.0005 mL, 0.0004 mL, 0.0003 mL, 0.0002 mL, or 0.0001 mL, and subvalues and subranges encompassed within the listed range of values. In some embodiments, such unit dose has a total volume of more than 0.2 mL and less than 500 mL, and subvalues and subranges encompassed within the listed range of values. In some embodiments, such unit dose has a total volume of less than 0.1 mL. In some embodiments, such unit dose has a total volume of less than 0.1 mL. In some embodiments, such unit dose has total volume of 0.1-0.2 mL (inclusive of 0.1 mL and 0.2 mL). In some embodiments, such unit dose has total volume of less than 0.1 and greater than 0.2 mL.

In some embodiments, a composition or unit dose has a total volume that is greater than 0.0001 mL, 0.0005 mL, 0.001 mL, 0.005 mL, 0.01 mL, 0.05 mL, 0.1 mL, 0.5 mL, 1 mL, 5 mL, 10 mL, 50 mL, or 100 mL per target site, and subvalues and subranges encompassed within the listed range of values.

In some embodiments, the composition or unit dose has a total volume in the range of 0.0001-500 mL, 0.0005-400 mL, 0.001-300 mL, 0.005-200 mL, 0.01-100 mL, 0.05-90 mL, 0.06-80 mL, 0.07-70 mL, 0.08-60 mL, 0.09-50 mL, 0.1-40 mL, 0.2-30 mL, 0.3-29 mL, 0.4-28 mL, 0.5-27 mL, 0.6-26 mL, 0.7-25 mL, 0.8-24 mL, 0.9-23 mL, 10-22 mL, 11-21 mL, 12-20 mL, 13-19 mL, 14-18 mL, or 15-17 mL per target site, and subvalues and subranges encompassed within the listed range of values.

Other embodiments contemplate administration of a total volume of a composition that is in the range of 0.01-30 mL, 0.02-20 mL, or 0.03-10 mL of total volume of a composition per target site. Other embodiments contemplate administration of 0.2-500 mL of total solution to a target site, 0.1-0.2 mL total solution to a target site, less than 0.1 mL, and subvalues and subranges encompassed within the listed range of values.

The unit dose will depend, in part, on the target area, amount of fat, and desired result.

Relative amounts of the active ingredient, the pharmaceutically acceptable and/or cosmetically acceptable carrier, and/or any additional ingredients in a pharmaceutical or cosmetic composition of the invention will vary, depending upon the identity, size, and/or condition of the subject treated and further depending upon which composition is to be administered.

In another embodiment of the present invention, the medical composition contains pharmaceutically acceptable excipients. In some embodiments, the cosmetic composition comprises cosmetically acceptable excipients.

Pharmaceutically acceptable excipients and/or cosmetically acceptable excipients used in the manufacture of provided pharmaceutical compositions or cosmetic compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, and perfuming agents may also be present in the composition.

Exemplary surface active agents and/or emulsifiers include lipids/natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Dosage forms for topical and/or transdermal administration of an active ingredient may include ointments, pastes, creams, lotions, gels, powders, solutions, sprays, inhalants and/or patches. Generally, the active ingredient is admixed under sterile conditions with a pharmaceutically acceptable and/or cosmetically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

In addition, injectable, including intradermal or transdermal injections are contemplated. Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate powder forms through the outer layers of the skin to the dermis are suitable. Alternatively or additionally, conventional syringes can be used in the classical mantoux method of intradermal administration. Administration may also be performed by microneedle(s).

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 0.01% to about 1% to about 10% (w/w) active ingredient, although the concentration of the active ingredient can be as high as the solubility limit of the active ingredient in the solvent. Formulations for topical administration may further comprise one or more of the additional ingredients described herein.

Although the descriptions of pharmaceutical or cosmetic compositions provided herein are principally directed to pharmaceutical or cosmetic compositions which are suitable for administration to humans, it will be understood by the skilled artisan that such compositions are generally suitable for administration to animals of all sorts. Modification of pharmaceutical or cosmetic compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in Remington: The Science and Practice of Pharmacy 21st ed., Lippincott Williams & Wilkins, 2005.

It will be also appreciated that the active ingredient can be administered in combination with one or more additional therapeutically active agents ("agents" or "active agents"). The compound or composition can be administered concurrently with, prior to, or subsequent to, one or more additional agents. In general, the active ingredient and each additional active agent will be administered at a dose and/or on a time schedule determined for the ingredient and agent. In will further be appreciated that the active ingredient and active agent utilized in this combination can be administered together in a single composition or administered separately in different compositions. The particular combination to employ in a regimen will take into account compatibility of the active ingredient with the active agent and/or the desired therapeutic effect to be achieved. In general, it is expected that additional active agents utilized in combination be utilized at levels that do not exceed the levels at which they are utilized individually. In some embodiments, the levels utilized in combination will be lower than those utilized individually.

The active ingredient can be administered in combination with active agents that improve their bioavailability, reduce and/or modify their metabolism, inhibit their excretion, and/or modify their distribution within the body. It will also be appreciated that therapy employed may achieve a desired effect for the same disorder (for example, an active ingredient can be administered in combination with an anti-inflammatory and/or anti-depressive agent, etc.), and/or it may achieve different effects (e.g., control of adverse side-effects).

In yet another embodiment of the present invention the medical composition contains one or more additional active ingredients. In some embodiments, the cosmetic composition contains one or more additional active ingredients. One or more additional active ingredients can include anti-inflammatory agents such as a steroidal anti-inflammatory agent or a non-steroidal anti-inflammatory agent; analgesics and dispersion agents such as hyaluronidase or collagenase.

In certain embodiments, the above methods comprise the administering of one or more additional compounds described herein or a pharmaceutically acceptable salt, hydrate, solvate, stereoisomer, polymorph, tautomer, or isotopically enriched derivative thereof.

In some embodiments, the subject or patient is a mammal. Such a mammal may be a human or an animal such as a primate (e.g., a monkey, a chimpanzee, etc.), a domesticated animal (e.g., a dog, a cat, a horse, etc.), a farm animal (e.g., goat, sheep, pig, cattle, etc.), or laboratory animal (e.g., a mouse, rat, etc.). In an embodiment of the present invention, the subject or patient is a human. As used herein, and unless otherwise indicated, "patient" is used interchangeably with "subject."

Methods for Reducing Body Fat

In certain embodiments, the present invention provides a method of reducing body fat in a subject, comprising administering locally to a subject in need thereof one or more compounds described herein, or a pharmaceutically acceptable salt, hydrate, solvate, stereoisomer, polymorph, tautomer, isotopically enriched derivative, or prodrug thereof.

Fat reduction can include reducing fat as measured by at least one of volume, size, mass, bulk, density, amount, and/or quantity. The present invention is expected to reduce fat by greater than or equal to 75%, greater than or equal to 70%, greater than or equal to 60%, greater than or equal to 50%, greater than or equal to 40%, greater than or equal to 30%, greater than or equal to 25%, greater than or equal to 20%, greater than or equal to 15%, greater than or equal to 10%, or greater than or equal to 5% relative to baseline. For example, fat reduction can also include reducing fat cell amount (for example, fat cell number), reducing fat cell volume, reducing fat cell maturation, and/or dedifferentiating a fat cell.

In certain embodiments, the body fat is local, e.g., concentrated on the abdomen, chest, back, breast, buttocks, hips, thighs, legs, knees, arms, chin, neck and/or face. In certain embodiments, the body fat is local, e.g., concentrated on the abdomen, chest, breast, buttocks, hips, thighs, legs, knees, arms, chin, neck and/or face. In some embodiments, the body fat is concentrated on the abdomen. In some embodiments, the body fat is concentrated on the chest. In some embodiments, the body fat is concentrated on the back. In some embodiments, the body fat is concentrated on the breast. In some embodiments, the body fat is concentrated on the buttocks. In some embodiments, the body fat is concentrated on the hips. In some embodiments, the body fat is concentrated on the thighs. In some embodiments, the body fat is concentrated on the legs. In some embodiments, the body fat is concentrated on the knees. In some embodiments, the body fat is concentrated on the arms. In some embodiments, the body fat is concentrated on the chin. In some embodiments, the body fat is concentrated on the neck. In some embodiments, the body fat is concentrated on the face. In some embodiments, the body fat is concentrated on the ankles. In some embodiments, the body fat is concentrated on the upper arms. In some embodiments, the body fat is concentrated on the forearms.

In certain embodiments, the subject suffers from or is likely to suffer from obesity, excess fat on the breast, gynecomastia, drug-induced obesity, hypothyroidism, pseudohypoparathyroidism, hypothalamic obesity, polycystic ovarian disease, depression, binge eating, postpartum obesity, obesity associated with smoking cessation, Prader-Willi syndrome, Bardet-Biedl syndrome, Cohen syndrome, Down syndrome, Turner syndrome, growth hormone deficiency, growth hormone resistance, leptin deficiency or resistance, Cushing syndrome, pseudo-Cushing syndrome, hypertrophy of dorsocervical fat/dorsocervical fat hypertrophy ("buffalo hump"), moon facies, lipoma, or excess fat on the chin. In some embodiments, the subject suffers from or is likely to suffer from obesity, gynecomastia, drug-induced obesity, hypothyroidism, pseudohypoparathyroidism, hypothalamic obesity, polycystic ovarian disease, depression, binge eating, postpartum obesity, obesity associated with smoking cessation, Prader-Willi syndrome, Bardet-Biedl syndrome, Cohen syndrome, Down syndrome, Turner syndrome, growth hormone deficiency, growth hormone resistance, leptin deficiency or resistance, Cushing syndrome, pseudo-Cushing syndrome, hypertrophy of dorsocervical fat/dorsocervical fat hypertrophy ("buffalo hump"), moon facies, or lipoma. In some embodiments, the subject suffers from or is likely to suffer from excess fat on the breast, excess fat on the chin, excess fat on the chest, excess fat on the back, excess fat on the buttocks, excess fat on the hips, excess fat on the thighs, excess fat on the legs, excess fat on the knees, excess fat on the arms, excess fat on the neck, or excess fat on the face.

In certain embodiments, the route of administration is selected from the group consisting of topical, subcutaneous, intradermal, and intralesional. In certain embodiments, the route of administering is topical. In certain embodiments, the site of administering is selected from the group consisting of the skin, the eye, or a mucosal membrane. In certain embodiments, the route of administering is selected from the group consisting of subcutaneous, intradermal, and intralesional. In certain embodiments, the administering is to a body part selected from the group consisting of the abdomen, chest, back, breast, buttocks, hips, thighs, legs, knees, arms, chin, neck, and face. In some embodiments, the body part is the abdomen. In some embodiments, the body part is the chest. In some embodiments, the body part is the back. In some embodiments, the body part is the breast. In some embodiments, the body part is the buttocks. In some embodiments, the body part is the hips. In some embodiments, the body part is the thighs. In some embodiments, the body part is the legs. In some embodiments, the body part is the knees. In some embodiments, the body part is the arms. In some embodiments, the body part is the chin. In some embodiments, the body part is the neck. In some embodiments, the body part is the face. In certain embodiments, the administering is to a body part selected from the group consisting of the abdomen, chest, breast, buttocks, hips, thighs, legs, knees, arms, chin, neck, and face. In certain embodiments, the topical administration is transdermal administration. In certain embodiments, the administering is to a fat depot located at the abdomen, chest, back, breast, buttocks, hips, thighs, legs, knees, arms, chin, neck, or face.

In certain embodiments, the subject has excess body fat as a side effect of medication (e.g., for example, sulfonylureas, antidepressants, monoamine oxidase inhibitors, selective serotonin reuptake inhibitors, oral contraceptives, insulin or a form of insulin, risperidone, clozapine, and thiazolidinediones).

In certain embodiments, the subject has excess body fat due to changes in hormonal status (e.g., as a result of physiologic changes such as pregnancy or menopause).

In certain embodiments, the subject with excess body fat is undergoing or has recently undergone smoking cessation.

In certain embodiments, the subject has body fat of cosmetic significance, for example, due to age-related orbital fat prolapse or descent of the malar fat pads.

This aspect of invention may also be useful as an adjunct to any of various kinds of surgery, whether used in the pre-operative, peri-operative, or post-operative period. The invention further contemplates uses preceding abdominal, thoracic, oncologic, endocrine, neurologic, transplant, and dermatologic surgery, whereby surgical exposure may be improved; and preceding or following orthopedic procedures, whereby surgical exposure as well as post-operative recovery may be improved.

Throughout the description, where compositions are described as having, including, or comprising specific components, or where processes are described as having, including, or comprising specific process steps, it is contemplated that compositions of the present invention may also consist essentially of, or consist of, the recited components, and that the processes of the present invention may also consist essentially of, or consist of, the recited processing steps. Further, it should be understood that the order of steps or order for performing certain actions are immaterial so long as the invention remains operable. Moreover, two or more steps or actions may be conducted simultaneously.

Para. A. A method of reducing subcutaneous fat comprising administering a topical or injectable composition containing a steroid chosen from the group comprising Pregnenolone or steroids derived therefrom.

Para. B. A method of reducing subcutaneous fat comprising administering a topical or injectable composition containing an alpha/beta adrenergic ligand.

Para. C. The method of Para. B, wherein the composition comprises Phentolamine.

Para. D. A method of reducing subcutaneous fat comprising administering a topical or injectable composition containing a statin.

Para. E. The method of Para. D, wherein the composition comprises lovastatin.

Para. F. A composition comprising one or more pharmaceutically acceptable excipients and a steroid derived from Pregnenolone.

Para. G. A composition comprising one or more pharmaceutically acceptable excipients and Pregnenolone.

Para. H. A composition comprising one or more pharmaceutically acceptable excipients and an alpha/beta adrenergic ligand.

Para. I. The composition of Para. H wherein the composition comprises Phentolamine Para. J. A composition comprising one or more pharmaceutically acceptable excipients and a statin.

Para. K. The composition of Para. J wherein the composition comprises lovastatin.

Para. L. A composition wherein the active is chosen from the group of Phentolamine, lovastatin, and Pregnenolone.

Para. M. A topical composition of Paras. F-L.

Para. N. An injectable composition of Paras. F-L.

Para. O. A composition of Paras. F-N wherein more than one active is present.

Para. P. The topical composition of Paras. F-M additionally comprising the excipients transcutol or ethanol.

Para. Q. The topical composition of Para. P containing transcutol and ethanol as excipients.

In light of the foregoing description, the specific non-limiting examples presented below are for illustrative purposes and not intended to limit the scope of the invention in any way.

EXAMPLES

Example 1: Effect of Statins on Human Mature Adipocytes

Figure 2:
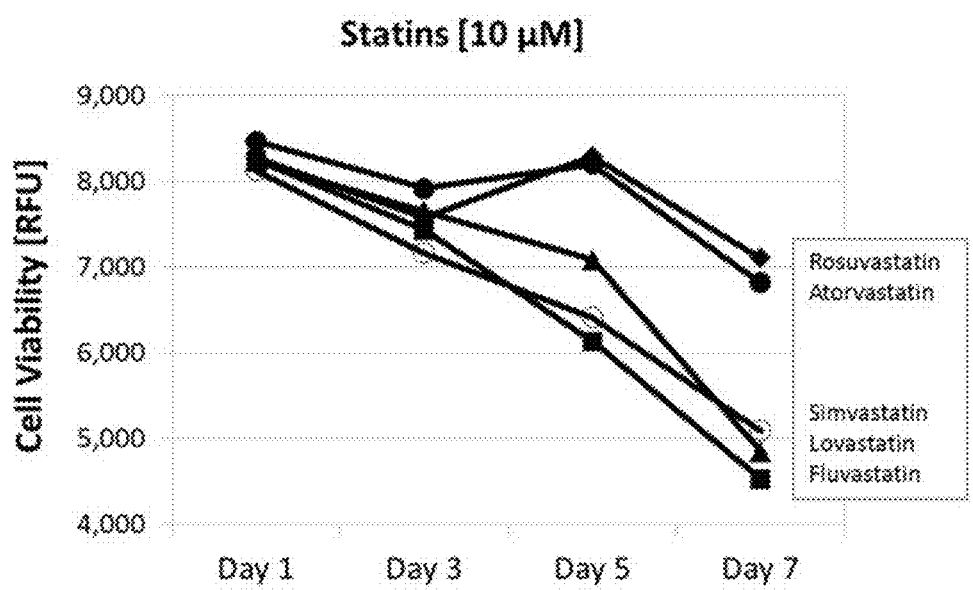
FIG. 2 depicts reduction in cell viability for different statins at 10 µM.
Figure 3:
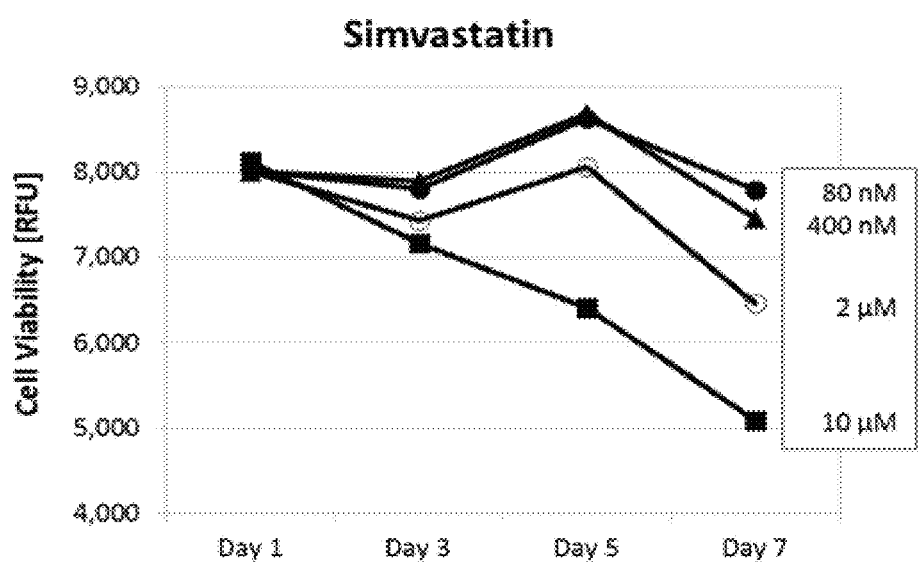
FIG. 3 depicts reduction in cell viability for various doses of simvastatin.
Figure 4:
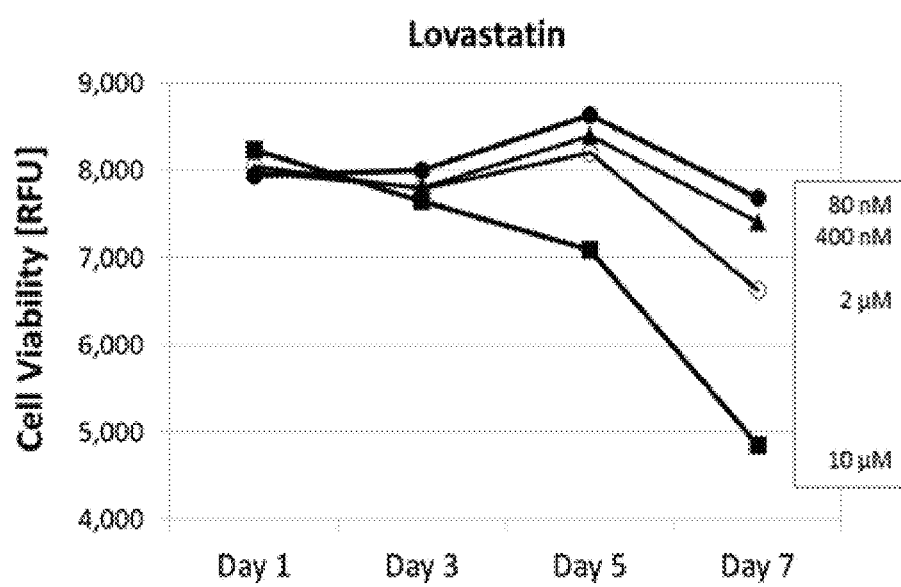
FIG. 4 depicts reduction in cell viability for various doses of lovastatin.
Figure 5:
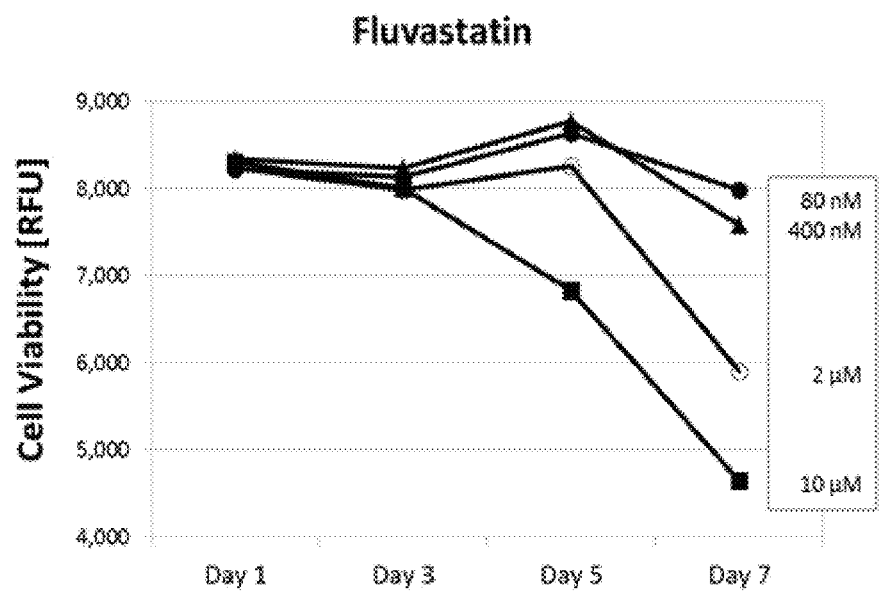
FIG. 5 depicts reduction in cell viability for various doses of fluvastatin.

Human pre-adipocytes (Lonza, Allendale, N.J.) were differentiated into mature adipocytes according to the supplier's instructions. Mature adipocytes in maintenance medium (Zen-Bio, Research Triangle Park, N.C.) were treated with different statins (Sigma, St. Louis, Mo.) for 7 days over a range of concentrations. Cell viability was measured at Day 1, 3, 5, and 7 using the ALAMARBLUE® assay (Invitrogen, Carlsbad, Calif.). All tested statins showed a reduction in cell viability over time. FIG. 2 shows statin treatment at 10 µM. Lovastatin, simvastatin and fluvastatin were more cytotoxic than rosuvastatin and atorvastatin. All tested statins have a dose-dependent cytotoxic effect (e.g., as shown for simvastatin in FIG. 3, lovastatin in FIG. 4, and fluvastatin in FIG. 5).

Figure 6:
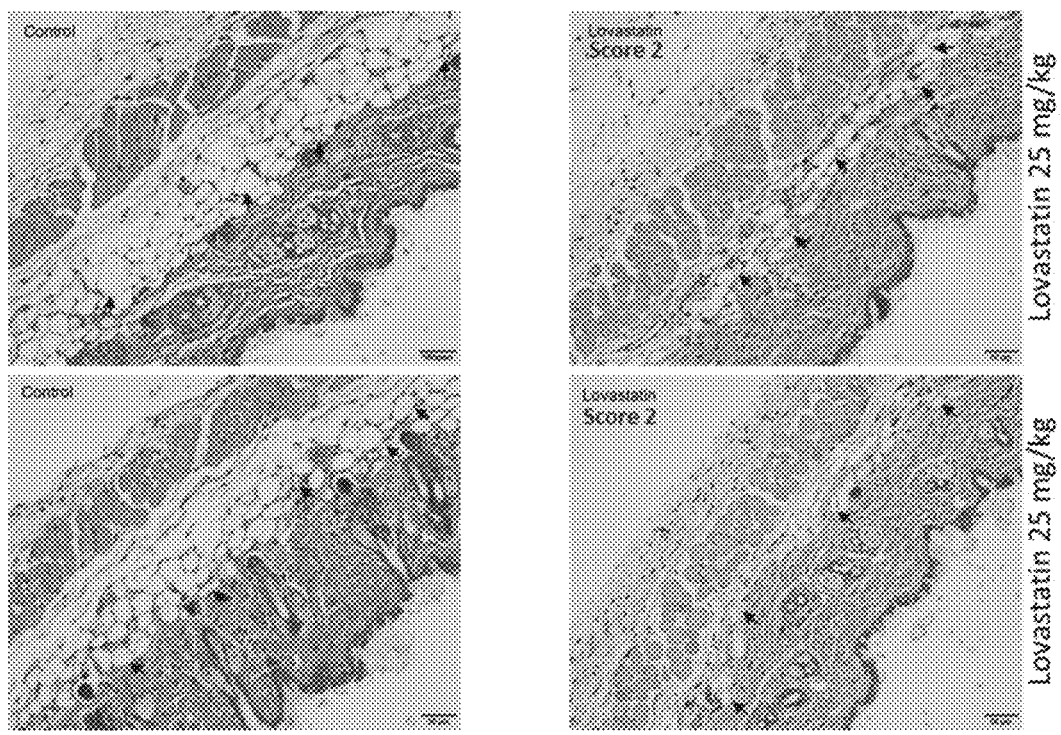
FIG. 6 depicts histology pictures of skin samples from two mice after intraperitoneal (IP) injection of lovastatin at 25 mg/kg.
Figure 7:
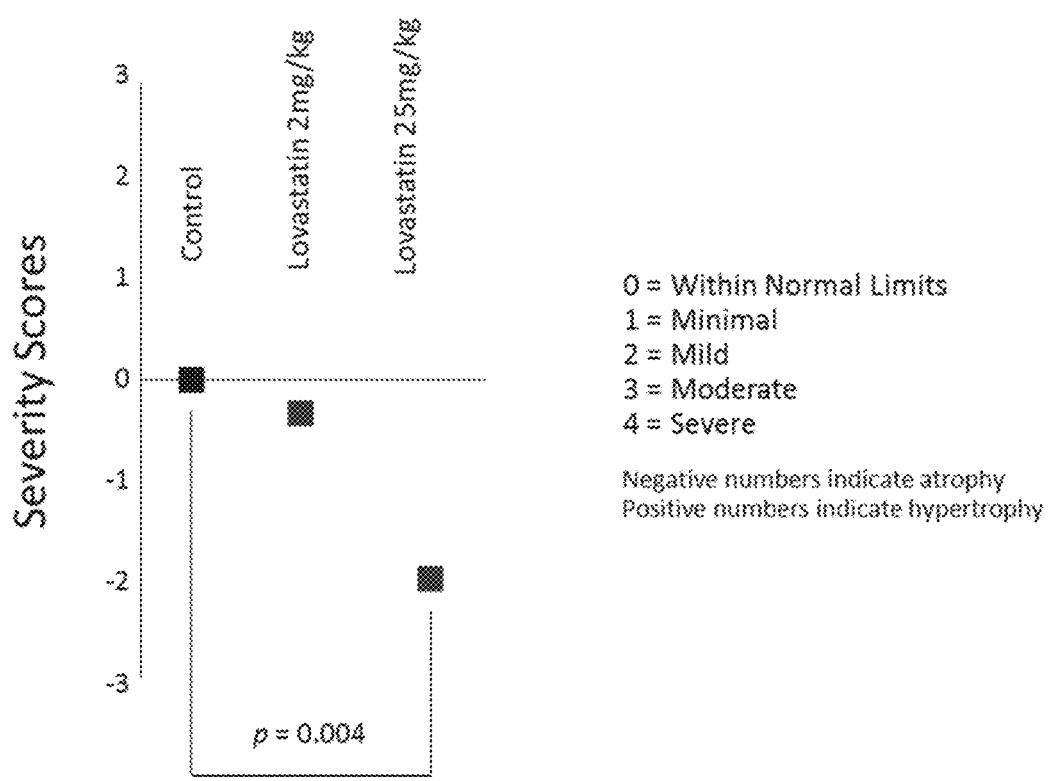
FIG. 7 depicts severity scores for subcutaneous fat atrophy from a murine study involving intraperitoneal injection of lovastatin.

Example 2: Systemic Administration of Lovastatin in Mice and Effect on the Subcutaneous Fat Layer Two groups of five 6 to 8-week old female BALB/cAnNCrl mice were injected intra-peritoneally with either 2 or 25 mg/kg/day lovastatin for 28 consecutive days. Three untreated mice were used as reference animals. On Day 29, all animals were sacrificed and histopathological examination of the dorsal lumbar skin was performed. Based on the absence of noteworthy clinical observations and effects on body weight, lovastatin administration was generally well tolerated. Intraperitoneal injection of lovastatin at 25 mg/kg caused significant fat layer atrophy as seen in representative skin sections from two different animals (FIG. 6). The severity of subcutaneous fat atrophy was scored on a scale ranging from normal (score of "0") to severe (score of "4"). The group average for the two lovastatin doses is shown in FIG. 7.

Figure 8:
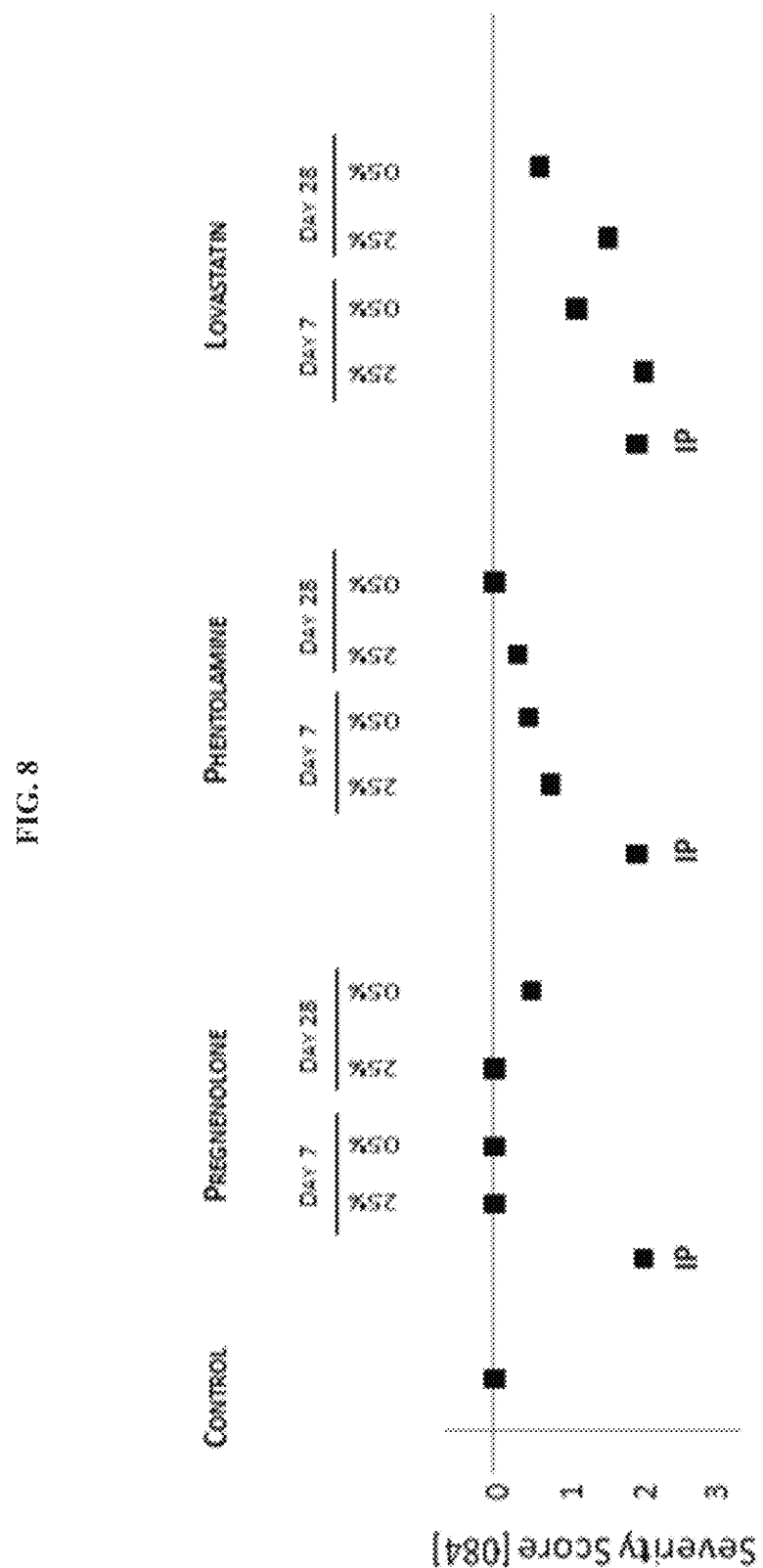
FIG. 8 depicts mean subcutaneous fat reduction in after 7 or 28 days of daily topical or intraperitoneal administration of pregnenolone, phentolamine or lovastatin in female BALB/cAnNCrl mice.

Example 3: Reduction in Subcutaneous Fat after 7 or 28 Days of Daily Topical or Intraperitoneal (IP) Administration of Pregnenolone, Phentolamine or Lovastatin in Female BALB/cAnNCrl Mice Female BALB/cAnNCrl mice were divided into five groups of three mice/group and seven groups of eight mice/group. Mice in Group 1 were age-matched, untreated pre-study reference animals, and mice in Group 2 were age-matched, untreated Day 29 reference animals. 3 groups of mice received 25 mg/kg of either pregnenolone (Group 5), phentolamine (Group 8), or lovastatin (Group 11) via IP administration for 28 consecutive days. 3 animals in Groups 3, 4, 6, 7, 9, 10, and 12 received topical doses of 2.5% pregnenolone (Group 3), 0.5% pregnenolone (Group 4), 2.5% phentolamine (Group 6), 0.5% phentolamine (Group 7), 2.5% lovastatin (Group 9), 0.5% lovastatin (Group 10), or vehicle (Group 12) for seven consecutive days while the remaining 5 animals in each Group 3, 4, 6, 7, 9, 10, and 12 received the same treatment for 28 consecutive days. Mid-scapular skin was collected from each animal and histopathological examination was performed to determine the effects of the test articles on subcutaneous adipose deposition and skin thickness. Severity scores (group averages) are shown in FIG. 8.

Pregnenolone: Atrophy of subcutaneous adipose tissue was present in skin of all mice that received intraperitoneal administration of 25 mg/kg of pregnenolone for 28 days. Atrophy was also present in a one mouse that received topical application of 0.5% pregnenolone for 28 days.

Phentolamine: Atrophy of subcutaneous adipose tissue was present in skin of all mice that received intraperitoneal administration of 25 mg/kg of phentolamine for 28 days. Atrophy was also present in mice that received 0.5% or 2.5% phentolamine for 7 days and in one mouse that received 2.5% phentolamine for 28 days.

Figure 9:
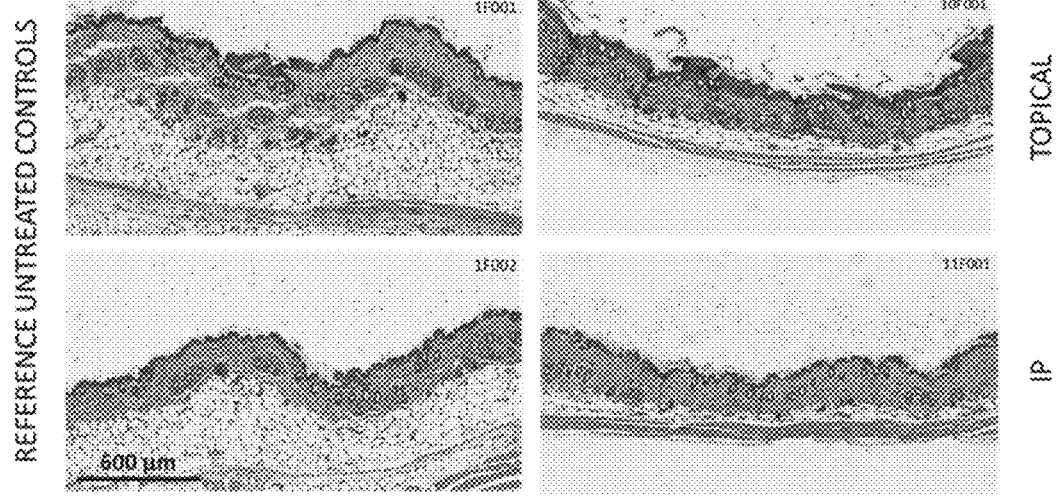
FIG. 9 depicts histology pictures of skin samples from mice after intraperitoneal injection or topical administration of lovastatin.

Lovastatin: Atrophy of subcutaneous adipose tissue was present in skin of all mice that received intraperitoneal administration of 25 mg/kg of lovastatin for 28 days. Atrophy was also present in all mice that received 2.5% lovastatin for 7 or 28 days or 2.5% lovastatin for 7 days. Only one mouse in the group that received 0.5% Lovastatin for 28 days showed subcutaneous fat atrophy. Select histology data, comparing the effect of lovastatin on the thickness of the subcutaneous adipose tissue is shown in FIG. 9.

Example 4: Subcutaneous Injection of Lovastatin in Minipigs

A Gottingen minipig is injected subcutaneously with lovastatin at doses ranging from 0.1 to 5 mg/cm² daily or twice daily for 7 to 28 days. Injections are administered 1 cm apart from each other in a volume of 200 µL to cover a 2 cm×2 cm area. At the end of the study, full thickness skin samples are prepared for histology examination and immunostaining and compared to untreated adjacent reference areas. Lovastatin treatment is expected to eliminate adipocytes and reduce the thickness of the fat layer.

Example 5: Lovastatin Treatment of Human Skin Samples

Human skin samples are collected from patients undergoing abdominoplasty surgery. The skin samples are mounted into modules and inserted in cell culture plates containing lovastatin at concentrations ranging from 50 nM to 50 µM. After 7-10 days in culture, the modules are disassembled and the treated skin is sectioned for histology and immunostaining examination. Weight and length measurements of the subcutaneous fat layer as well as apoptosis markers are expected to show that lovastatin treatment eliminates adipocytes and reduces the thickness of the fat layer compared to the untreated reference samples.

Example 6: Cosmetic Treatment of a Human Subject by Direct Injection into the Subcutaneous Fat Layer A sterile solution containing lovastatin at doses ranging from 0.1 to 5 mg/cm² is administered to a human subject seeking corrective aesthetic contouring of an unwanted fat deposit by direct injection into the subcutaneous fat layer of the human subject. Injections are administered 1-5 cm apart from each other in a volume of 200-1000 µL until the desired area has been fully treated. Multiple treatment cycles can be administered until the desired effect is obtained. Treatment cycles are administered one month apart from each other, up to a maximum of 6 treatments. Lovastatin treatment is expected to eliminate adipocytes and reduce the thickness of the fat layer to an extent that is aesthetically pleasing to the subject.

Example 7: Cosmetic Treatment of a Human Subject by Topical Application

Aesthetic reduction of unwanted fat is achieved by treating a human subject with a topical formulation of lovastatin at strengths ranging from 0.5% w/v to 5% w/v. The lovastatin cream is applied by hand once daily onto the treatment area with gentle rubbing until absorbed. Subcutaneous fat reduction of the treated area is expected to be noticeable after daily application for 7 days and treatment can be continued until the desired effect is observed.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All patents, patent applications, and literature references cited herein are incorporated herein by reference. Definitions that are contained in text incorporated by reference are excluded to the extent that they contradict definitions in this disclosure. The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of reducing subcutaneous fat in a subject in need thereof, the method comprising administering to the subject (i) a topical composition comprising a statin administered to the skin.

2. The method of claim 1, wherein the statin is selected from the group consisting of lovastatin, simvastatin, and fluvastatin.

3. The method of claim 1, wherein the statin is lovastatin.

4. The method of claim 1, wherein the statin is simvastatin.

5. The method of claim 1, wherein the statin is fluvastatin.

6. The method of claim 1, wherein the method excludes surgical intervention.

7. The method of claim 1, wherein the topical composition further comprises one or more additional active compounds.

8. The method of claim 7, wherein the one or more additional active compounds are selected from anti-inflammatory agents, analgesics, and dispersion agents.

9. The method of claim 1, wherein the topical composition further comprises one or more pharmaceutically acceptable and/or cosmetically acceptable excipients.

10. The method of claim 1, wherein the subcutaneous fat is located on the abdomen, chest, back, breast, buttocks, hips, thighs, legs, knees, arms, chin, neck, or face.

11. The method of claim 1, wherein the subject suffers from obesity, excess fat on the breast, gynecomastia, drug-induced obesity, hypothyroidism, pseudohypoparathyroidism, hypothalamic obesity, polycystic ovarian disease, depression, binge eating, postpartum obesity, obesity associated with smoking cessation, Prader-Willi syndrome, Bardet-Biedl syndrome, Cohen syndrome, Down syndrome, Turner syndrome, growth hormone deficiency, growth hormone resistance, leptin deficiency or resistance, Cushing syndrome, pseudo-Cushing syndrome, hypertrophy of dorsocervical fat/dorsocervical fat hypertrophy ("buffalo hump"), moon facies, lipoma, or excess fat on the chin.

* * * * *